United States Patent [19]

Baasner et al.

[11] Patent Number: 4,588,837

[45] Date of Patent: May 13, 1986

[54] PROCESS FOR THE PREPARATION OF FLUOROCARBOXYLIC ACIDS

[75] Inventors: Bernd Baasner, Leverkusen; Erich Klauke, Odenthal; Reinhard Lantzsch, Leverkusen, all of Fed. Rep. of Germany

[73] Assignee: Bayer Aktiengesellschaft, Leverkusen, Fed. Rep. of Germany

[21] Appl. No.: 632,135

[22] Filed: Jul. 18, 1984

[30] Foreign Application Priority Data

Jul. 21, 1983 [DE] Fed. Rep. of Germany ....... 3326210

[51] Int. Cl.⁴ .................... C07C 51/097; C07C 53/18
[52] U.S. Cl. .................................................. 562/605
[58] Field of Search ............................... 562/602, 605

[56] References Cited

PUBLICATIONS

Dokl. Akad. Nauk. SSSR (149), pp. 222–225 (1963); Titov.
Industrial and Engineering Chem., vol. 31, pp. 118–120, (1939); Lippincott et al.
Isvest. Akad. Nauk. SSSR, 1963, pp. 1794–1797; Knunyants et al., II.
Isvest. Akad. Nauk. SSSR, Ser. Khim., 1963, pp. 1798–1799; Knunyants et al., I.
Tetrahedron, vol. 26, p. 5737, (1970); Bissell et al.
Beilsteins Handbuch der Organischen Chemie, 4. Auflage, 2, Ergänzungswerk, 2. Band, Springer Verlag, Berlin, 1942, Seite 186, Zeilen 1–3.

Primary Examiner—Natalie Trousof
Assistant Examiner—Patricia M. Scott
Attorney, Agent, or Firm—Sprung Horn Kramer & Woods

[57] ABSTRACT

Fluorocarboxylic acids are prepared by metering fluoronitroaliphatic compounds into a mineral acid which has been initially introduced.

1 Claim, No Drawings

PROCESS FOR THE PREPARATION OF FLUOROCARBOXYLIC ACIDS

The invention relates to the preparation of fluorocarboxylic acids from fluoronitroaliphatic compounds.

It is known that aliphatic carboxylic acids can be prepared by boiling the corresponding primary nitroparaffins under reflux with 85% strength sulphuric acid (Ind. Eng. Chem. Vol. 31, 118–120 (1939)). However, this known reaction cannot be transferred to primary nitro-paraffins which are substituted by fluorine, since the fluoronitroaliphatic compounds undergo decomposition and side reactions under the conditions maintained for this reaction, in particular by reason of the long reaction times. In particular, oxidation reactions and hydrolysis of the halogen atoms bonded in the 2-position take place.

The preparation of trifluoroacetic acid by heating a mixture of 2,2,2-trifluoro-1-nitroethane, concentrated sulphuric acid and water under pressure in an autoclave at 200° C. for 3 hours with shaking is known from Isvest. Akad. Nauk SSSR, Ser. Khim. 1963, 1798–1799 (Engl.). This process, which cannot be transferred to other nitroaliphatic compounds substituted by fluorine, is carried out under very drastic conditions. In contrast, 2,2,2-trifluoro-1-nitroethane remains unchanged when the mixture is heated at 100° C. under atmospheric pressure for 10 hours.

A process for the preparation of fluorocarboxylic acids by reacting fluoronitroaliphatic compounds of the formula

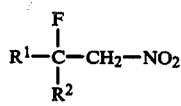

in which

R$^1$ and R$^2$ are identical or different and denote hydrogen, fluorine, chlorine, bromine or lower alkyl, with mineral acids has been found, which process is characterised in that the mineral acid is initially introduced and the fluoronitroaliphatic compound is metered in.

The process according to the invention can be described by the equation of reaction below:

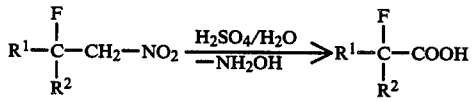

In this context, lower alkyl generally denotes a straight-chain or branched hydrocarbon radical having 1 to, say, 6 carbon atoms. The following lower alkyl radicals may be mentioned as examples: methyl, ethyl, propyl, isopropyl, butyl, isobutyl, pentyl, isopentyl, hexyl and isohexyl. The preferred lower alkyl radicals are the methyl and ethyl radicals.

Examples of mineral acids for the process according to the invention are sulphuric acid, hydrochloric acid, hydrobromic acid, phosphoric acid, nitric acid and perchloric acid.

Preferred mineral acids for the process according to the invention are sulphuric acid and phosphoric acid.

Water is necessary for the reaction according to the invention, and this is generally introduced together with the mineral acid, as an aqueous mineral acid. The proportion of water is generally 1 to 10 mol, preferably 1.2 to 5 mol, relative to 1 mol of the fluoronitroaliphatic compound.

The proportion of the mineral acid is generally 1 to 100 mol, preferably 1 to 20 mol, relative to 1 mol of the fluoronitroaliphatic compounds.

In general, the mineral acids introduced contain from 2 to 20% by weight, preferably from 3 to 10% by weight, of water.

Elevated pressure is not necessary for the process according to the invention.

The process according to the invention is carried out in the temperature range from 80° to 250° C., preferably from 100° to 200° C.

Fluoronitroaliphatic compounds for the process according to the invention are known per se. They can be prepared by, for example, reacting aliphatic carboxylic acids which contain nitro groups with SF$_4$/BF$_3$ (Tetrahedron 26, 5737 (1970)) or by reaction of olefins in anhydrous hydrogen fluoride with concentrated nitric acid (Dokl. Akad. Nauk SSSR (149), 222–5 (1963) (Engl.) and Isvest. Akad. Nauk SSSR 1963, 1794–7 (Engl.)).

The following fluoronitroaliphatic compounds may be mentioned as examples: 2-chloro-2,2-difluoronitroethane, 2,2-dichloro-2-fluoronitroethane, 2,2-difluoronitroethane, 2-chloro-2-fluoronitroethane, 2-bromo-2-fluoronitroethane, 2,2-difluoronitropropane and 2,2,2-trifluoronitroethane. 2,2,2-trifluoronitroethane is preferred for the process according to the invention.

The process according to the invention can be carried out as follows, for example:

The aqueous mineral acid is initially introduced and heated to the reaction temperature according to the invention. The fluoronitroaliphatic compound is added dropwise to, passed into, pumped into or passed together with an inert gas, such as nitrogen, into this heated aqueous mineral acid, while thoroughly mixing. This reaction takes place exothermically, and the rate of metering in is selected such that the fluoroaliphatic nitro compound reacts completely as it is metered in to give fluorocarboxylic acid.

After reaction is complete, the fluorocarboxylic acid can be distilled out under atmospheric pressure or reduced pressure (1 to 0.01 bar). The fluorocarboxylic acid can also be isolated, after the end of the reaction, by steam distillation or extraction with an inert organic solvent, such as dichloromethane or tetrachloromethane.

The acid content can be determined by, for example, titration.

Further purification can be carried out, where appropriate, by redistillation under reduced pressure or under normal pressure or by recrystallization.

In a preferred embodiment of the process according to the invention, the fluorocarboxylic acid being produced in the reaction is continuously removed from the reaction mixture during the reaction by, for example, distillation. Exposure to heat and thus the possibility of side reactions and decomposition reactions of the fluorocarboxylic acid can be largely avoided in this manner. It is also possible to arrange for the preparation of the fluorocarboxylic acid to be continuous by continuously and simultaneously metering fluoronitroaliphatic compounds and concentrated mineral acid into a reactor suitable for this purpose.

The hydroxylammonium sulphate which has been produced can be isolated by customary processes from the residue from the reaction. Thus, for example, ethanol can be added to the residue so that the hydroxylammonium sulphate precipitates. However, it is also possible to take up the residue in water, neutralize the excess acid and isolate the hydroxylammonium sulphate by concentrating this mixture.

Fluorocarboxylic acids of the formula

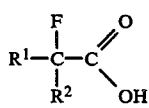

in which

R$^1$ and R$^2$ have the abovementioned meaning, can be prepared by the process according to the invention.

Fluorocarboxylic acids can be used as, for example, intermediates for herbicides (German Offenlegungsschrift No. 2,914,003). It is surprising that it is possible to prepare fluorocarboxylic acids by the process according to the invention, since, in contrast to statements in the literature, the reaction of 2,2,2-trifluoro-1-nitroethane with sulphuric acid and water can be carried out even at temperatures as low as 200° C. and under atmospheric pressure, and thus it has become possible for the first time to transfer this reaction to a commercial scale which can also be carried out continuously in industry.

Furthermore and surprisingly, no hydrolysis of the halogen atoms bonded in the 2-position takes place in the process according to the invention.

EXAMPLE 1

Chlorodifluoroacetic acid from 2-chloro-2,2-difluoronitroethane 220 ml of 90% strength sulphuric acid were heated to an internal temperature of 125°–130° C. 72.8 g (0.5 mol) of 2-chloro-2,2-difluoronitroethane were added dropwise, with stirring, in 30 minutes, the mixture was then stirred for 30 minutes, and the chlorodifluoroacetic acid was distilled out at 114° to 130° C. After redistillation at boiling point 119° to 122° C., 57.6 g (88%) of product were obtained, n$_D^{20}$: 1.3585.

The following were prepared in analogous procedures:

EXAMPLE 2

From 0.5 mol of 2,2-dichloro-2-fluoronitroethane, 60 g (82%) of dichlorofluoroacetic acid, boiling point 156° to 159° C., n$_D^{20}$1.4171

EXAMPLE 3

From 0.5 mol of 2,2-difluoronitroethane, 42.6 g (89%) of difluoroacetic acid, boiling point 133° to 136° C., n$_D^{20}$: 1.3435.

EXAMPLE 4

From 0.5 mol of 2-chloro-2-fluoronitroethane, 53.0 g (94%) of chlorofluoroacetic acid, boiling point 74° to 5° C./25 mbar, n$_D^{20}$: 1.4091.

EXAMPLE 5

From 2-bromo-2-fluoronitroethane, 48.2 g (61%) of bromofluoroacetic acid, boiling point 116 to 120° C./50 mbar, melting point 49° to 50° C.

EXAMPLE 6

From 2,2-difluoronitropropane, 46.7 g (85%) of difluoropropionic acid, boiling point 138° to 140° C., melting point 39° to 42° C.

EXAMPLE 7

Trifluoroacetic acid from 2,2,2-trifluoronitroethane 180 ml of 96% strength sulphuric acid were initially introduced and heated to an internal temperature of 130° to 135° C. 64.5 g (0.5 mol) of 2,2,2-trifluoronitroethane were added dropwise to this in about 150 minutes and at the same time the trifluoroacetic acid produced was continuously distilled out. After redistillation at boiling point 70° to 72° C., 46.8 g (82%) of product were obtained.

EXAMPLE 8

Trifluoroacetic acid from 2,2,2-trifluoronitroethane 200 ml of 95% strength sulphuric acid were initially introduced and heated to an internal temperature of 180°–190° C. 64.5 g (0.5 mol) of 2,2,2-trifluoronitroethane were metered into this heated acid in about 4 hours through an introduction tube which extended to the base of the reaction vessel, using a gentle stream of nitrogen. The trifluoroacetic acid produced was at the same time continuously distilled out over a short column. 51.9 g (91%) of product of boiling point 69.5°–71° C. were obtained.

What is claimed is:

1. A process for the preparation of trifluoroacetic acid which comprises introducing at 130° to 200° C. and at normal pressure 2,2,2-trifluoronitroethane into a sulfuric or phosphoric acid which contains 2 to 20% by weight of water, said introducing of the 2,2,2-trifluoronitroethane being at a rate corresponding to the rate of production of said trifluoroacetic acid and continuously removing the trifluoroacetic acid from the reaction mixture by distillation.

* * * * *